United States Patent [19]

Corvers et al.

[11] 4,417,053
[45] Nov. 22, 1983

[54] PROCESS FOR THE PREPARATION OF SUBSTITUTED GLYOXYLIC ACID DERIVATIVES

[75] Inventors: Antonius Corvers, Beek; Cornelis W. van den Broek, Schaesberg; Geertrudes H. Suverkropp, Geleen, all of Netherlands

[73] Assignee: Stamicarbon B.V., Geleen, Netherlands

[21] Appl. No.: 320,562

[22] Filed: Nov. 12, 1981

[30] Foreign Application Priority Data

Nov. 13, 1980 [NL] Netherlands .......................... 8006192

[51] Int. Cl.$^3$ ...................... C07C 69/76; C07D 213/50
[52] U.S. Cl. ....................................... 546/315; 549/72; 549/483; 560/51; 564/169; 546/341; 546/342
[58] Field of Search .......................... 560/51; 564/169; 260/347.3, 347.4; 546/315, 341; 549/72, 483

[56] References Cited

U.S. PATENT DOCUMENTS 3,173,933  3/1965  Hay ...................................... 260/413

OTHER PUBLICATIONS

Tsuruya et al., J. Mol. Catal., (1980), vol. 10(1), pp. 21-32.
Baer et al., J.A.C.S., (1945), vol. 67, pp. 1482-1483.
Hackh's Chemical Dictionary, p. 312, (1969).

Primary Examiner—Henry R. Jiles
Assistant Examiner—Bernard Dentz

[57] ABSTRACT

A process for preparing substituted glyoxylic acid derivatives by oxidizing with a molecular oxygen containing gas an amide or ester of a hydroxy acid in the presence of a catalytic amount of a cobalt compound.

8 Claims, No Drawings

PROCESS FOR THE PREPARATION OF SUBSTITUTED GLYOXYLIC ACID DERIVATIVES

This invention relates to a process for the preparation of substituted glyoxylic acid derivatives by the oxidation of the corresponding hydroxy derivative.

An example of such a reaction known in the art is the oxidation of a mandelic acid ester to the corresponding ester of phenylglyoxylic acid, which oxidation can be carried out with selenium dioxide or lead tetra-acetate as the oxidant (see page 127 of RODD's Chemistry of Carbon Compounds, 2nd edition, volume III part E, 1974, Elsevier Scientific Publishing Company). Another oxidant also known in the art for said oxidation is chromium trioxide (see European patent application 0.006.539).

A major disadvantage from the use of these above-mentioned oxidants is that a large amount of the metal compound is left over as waste.

The present invention now provides an improved process for the preparation of substituted glyoxylic acid derivatives in which no metal compound is obtained as waste.

The process according to this invention is distinguished by the features that, in combination, an amide or ester of a hydroxy acid of the general formula:

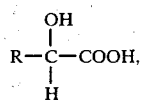

wherein R represents an (possibly substituted) aryl or heteroaryl group, is oxidized in the liquid phase, in the presence of cobalt as catalyst, with a molecular-oxygen-containing gas, and recovering from the reaction mixture the corresponding amide or the corresponding ester of a glyoxylic acid of the general formula:

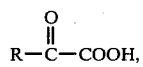

wherein R has the above-mentioned meanings.

It has now been found that the oxidation according to this invention can be carried out more rapidly than the oxidation in which the above-mentioned already known oxidants are employed, while, moreover, a higher degree of selectivity can be achieved. Furthermore, the product obtained is often pure enough to be suitable as such for further conversions, for instance, to an herbicide.

The favorable result of the process according to this invention is very surprising. The fact is that, if either the nitrile of the hydroxy acid or the hydroxy acid itself is oxidized in the same manner, a reaction mixture is obtained in which the desired keto compound is not at all, or hardly at all, present.

In the oxidation process according to this invention, various compounds may be used as starting materials. For instance, the aryl or heteroaryl (resonating heterocyclic radicals) group represented by R in the above general formula may be a phenyl, naphthyl, pyridyl, furyl or thienyl group, which groups can optionally be substituted with, for instance, one or more substituents from the group consisting of Cl, $NO_2$, alkoxy of from 1–8 carbon atoms and alkyl of from 1–8 carbon atoms.

Various esters can be employed as the ester of the hydroxy acid, for instance, those esters having, in the ester group, an alkyl group with from 1–8 carbon atoms, a cycloalkyl group with from 5–8 carbon atoms in the ring, a phenyl group or a naphthyl group. Alternatively, an amide may be used.

In employing the process according to this invention, the oxidation takes place in the liquid phase. If the compound to be oxidized can function as a solvent for the reaction mixture, the oxidation can in principle be carried out without solvent. Preferably, however, a solvent is used. Suitable solvents include saturated aliphatic monocarboxylic acids with from 2–8 carbon atoms, especially acetic acid. The acid employed as solvent may be only of a commercial grade and contain, for instance, 3% by weight of water. Esters of the said acids can also be used as solvents. The quantity of solvent may also vary. A quantity of solvent of from 0.5–15 g per gram of hydroxy derivative to be oxidized is very suitable.

The catalytic quantity of cobalt required in the reaction mixture can be obtained by introduction of a cobalt compound soluble in the reaction mixture, such as inorganic or organic cobalt salts, or by the formation of such a compound in situ. Preferably, a cobalt salt of a saturated aliphatic monocarboxylic acid with from 1–8 carbon atoms, specifically cobalt acetate (either di- and/or tetravalent cobalt), is dissolved in the reaction mixture, for instance, in a quantity corresponding with from 1–50 g cobalt per mole of compound to be oxidized. A very good result can be obtained if, in addition to the cobalt salt, an alkali metal bromide, is also present as a promoter in a quantity of, for instance, 0.5–20 g bromide per mole of compound to be oxidized. The catalyst and the promoter can be separated from the reaction mixture obtained, recycled, and be used again if so desired.

The oxidation according to the invention can be carried out at various temperatures, for instance, from 25° to 250° C. Preferably, the chosen temperature is between about 70° and about 150° C. The pressure as such as not critical. Use of a pressure higher than atmospheric pressure may be of advantage in large scale oxidations, for instance if acetic acid is used as solvent and air as the oxygen-containing gas. The fact is that in such a case the explosive range of the acetic acid vapor-nitrogen-oxygen system can be avoided by diluting the air with nitrogen or by employing a pressure higher than atmospheric.

The oxidation according to this invention can generally be carried out by methods known in the art for carrying out liquid phase oxidations with a molecular oxygen-containing gas. For instance, the gas may be passed through the reaction mixture for some time at the desired temperature, while the mixture is well stirred. In this process, different times may be chosen during which the reaction conditions are maintained.

The oxidation according to the invention will now be further elucidated in the following non-limiting Examples.

EXAMPLE I

Into a cylindrical reaction vessel with a capacity of 250 ml, provided with 4 baffle plates, stirrer, reflux condenser and air inlet tube, 4 g of cobalt(II) acetate.4-$H_2O$, 0.41 g of sodium bromide, 17 g of ethyl mandelate (0.094 mole) and 116 ml of acetic acid (99.5% by weight) were introduced.

The reaction mixture was heated to 90° C., after which air was passed in at a rate of 20.5 liters per hour. After the air had been passed in for 5 minutes, the temperature of the reaction mixture was 103° C. After air had been passed in for 25 minutes, the temperature of the reaction mixture was 97° C., and the introduction of the air was discontinued.

The reaction mixture thus obtained was subjected to a gas chromatographic analysis, which showed that the ethyl mandelate had been completely converted into the corresponding keto compound, with a selectivity of 96%.

The reaction mixture was subsequently poured out into 1 liter, of water, and the aqueous solution obtained was extracted with ether. The ether extract was neutralized with $NaHCO_3$ to a pH of about 8 and dried over $MgSO_4$. After evaporation of the ether under reduced pressure, 15.7 g light yellow product remained, which was the desired keto compound with a purity of 99% as determined by gas chromatographic analysis. The yield was 92% of theoretical.

COMPARATIVE EXAMPLES

In the same way as described in Example I, an attempt was made to oxidize mandelic acid per se. After air had been passed through for 2 hours and 15 minutes, the reaction mixture was analyzed, which showed that the mandelic acid had not been converted.

An attempt to oxidize the nitrile of mandelic acid (benzaldehyde-cyanohydrin) in the manner as described in Example I also failed to result in a keto compound. After air had been passed through for 15 minutes, the reaction mixture was found to contain, beside the initial product, benzaldehyde only, while, after air had been passed through for 1 hour, benzoic acid had been formed as well.

EXAMPLE II

In the manner as described in Example I, 16.6 g methyl mandelate (0.1 mole) was oxidized. After air had been passed in for 1 hour, a 100% conversion was reached, at a selectivity of 94%.

EXAMPLE III

Example I was repeated. The reaction temperature, however, was kept at 90° C. After air had been passed through for 33 minutes, a 100% conversion was found to have been reached, and the selectivity was 98%.

EXAMPLE IV

Repetition of Example I at a temperature of 110° had as a result that, after air had been passed through for 22 minutes, a 100% conversion had already been reached, and the selectivity was 98%.

EXAMPLE V

In the same way as described in Example I, 0.1 mole of mandelic acid amide was oxidized. After air had been passed through for 30 minutes, the conversion was 100% and the selectivity with respect to the corresponding keto-amide 81%.

EXAMPLE VI

In the manner as described in Example I, 0.25 mole ethyl mandelate was oxidized in 116 ml acetic acid with 4 g cobalt(II)acetate.$4H_2O$ and 0.41 g NaBr at a temperature of 100° C. After a period of 75 minutes, a conversion of 100% was reached, with the selectivity being 98%.

EXAMPLE VII

Example VI was repeated, except that NaBr was omitted. The oxidation process was much slower now. After 75 minutes, the conversion was 45% and the selectivity 81%.

EXAMPLE VIII

In the manner described in Example I, 18 g ethyl mandelate (0.1 mole) was oxidized. After air had been passed through for 30 minutes, the conversion was 100%, and the reaction mixture obtained was further processed as follows:

First, the acetic acid was distilled off under reduced pressure. Subsequently, 100 g water was added to the remaining residue, and the mixture was subjected to extraction with ether. The organic layer obtained in this process was washed with water and neutralized with $NaHCO_3$ to a pH of 8. After drying of the organic layer over $MgSO_4$, the ether was evaporated under reduced pressure. 17.3 g of the desired keto ester compound was obtained (yield 95%), which, according to a gas chromatographic analysis, had a purity of 98.6%.

EXAMPLE IX

The aqueous layer obtained in Example VIII during the extraction with ether, which layer contained the cobalt catalyst and the NaBr, was evaporated to dryness. To the residue of 4.7 g 18 g ethyl mandelate (0.1 mole) and 116 ml acetic acid (99.5% by weight) were added, after which the ethyl mandelate was oxidized in the manner described in Example I. After air had been passed through for 45 minutes, the reaction mixture was further processed in the manner described in Example VIII. 17.3 g keto compound was obtained (yield 92%), which as determined by a gas chromatographic analysis, had a purity of 95%. This shows the re-use of the cobalt catalyst and NaBr.

EXAMPLE X

In the manner described in Example I, 0.1 mole 2,4-dichloroethylmandelate was oxidized. After air had been passed through for 20 minutes, the conversion was 100% and the selectivity with respect to the desired keto compound was 93%. The keto compound obtained had a boiling point of 118° C. at a pressure of 27 Pa.

EXAMPLE XI

In the manner described in Example I, 0.1 mole of the ethyl ester of 4-methoxy-mandelic acid was oxidized. After air had been passed through for 20 minutes, the conversion was 100% and the selectivity with respect to the keto compound was 97%.

EXAMPLE XII

In the manner described in Example I, 0.1 mole of the ethyl ester of (2-thienyl)hydroxyacetic acid was oxidized. After air had been passed through for 30 minutes, a conversion of 100% was reached. After further processing of the reaction mixture, 16.4 g product was obtained containing 96% of the corresponding keto compound (yield 87%).

EXAMPLE XIII

In the manner described in Example I, 0.1 mole of the ethyl ester of (3-pyridyl)hydroxyacetic acid was oxidized. After air had been passed through for 2 hours and 20 minutes, the conversion was 97% and the selectivity with respect to the relative keto compound was 82%. The keto compound obtained had a boiling point of 90° C. at a pressure of 7 Pa.

EXAMPLE XIV

In the manner described in Example I, 0.1 mole of the ethyl ester of 4-nitromandelic acid was oxidized. After air had been passed through for 2 hours, a conversion of 96% was reached. The selectivity with respect to the relative keto compound was 60%. As by-product, the reaction mixture was found to contain 4-nitrobenzoic acid.

EXAMPLE XV

In the manner described in Example I, 0.1 mole of n-butyl mandelate was oxidized. After air had been passed through for 15 minutes, 100% conversion was reached. The selectivity with respect to the corresponding keto compound was 97%.

EXAMPLE XVI

In the manner described in Example I, 0.1 mole of the methyl ester of 4-carbomethoxy mandelic acid was oxidized. After air had been passed through for 40 minutes, 100% conversion was reached. The selectivity with respect to the corresponding keto compound was 93%.

EXAMPLE XVII

In the manner described in Example I, 0.1 mole of the ethyl ester of 4-ethoxy mandelic acid was oxidized. After air had been passed through for 30 minutes, 100% conversion was reached. The selectivity with respect to the desired keto compound was 92%.

EXAMPLE XVIII

In the manner described in Example I, 0.1 mole of the ethyl ester of 3-phenoxy mandelic acid was oxidized. After air had been passed through for 30 minutes, 100% conversion was reached. The selectivity with respect to the desired keto compound was 98%.

EXAMPLE XIX

In the manner described in Example I, 0.1 mole ethyl mandalate in 116 ml acetic acid was oxidized at a temperature of 100° C. with the aid of 2.7 g $CoBr_2.6H_2O$.

After air had been passed through for 35 minutes, 100% conversion was reached. The selectivity with respect to the keto compound concerned was 94%.

What is claimed is:

1. A process for the preparation of substituted glyoxylic acid derivatives by the oxidation of the corresponding hydroxy derivative, wherein an amide or ester of a hydroxy acid of the general formula:

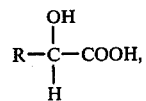

wherein R represents an (possible substituted) aryl or heteroaryl group, is oxidized in the liquid phase with molecular-oxygen-containing gas, in the presence of a catalytic amount of a cobalt compound, and recovering the corresponding amide or the corresponding ester of glyoxylic acid having the general formula:

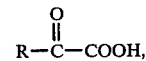

from the resulting reaction mixture.

2. A process according to claim 1, wherein said oxidation is carried out in a solvent.

3. A process according to claim 2, wherein said solvent is a saturated aliphatic monocarboxylic acid with from 2–8 carbon atoms.

4. Process according to any one of claims 1, 2 or 3, wherein the oxidation is carried out in the additional presence of an alkali metal bromide as promoter.

5. Process according to any one of claims 1, 2 or 3, wherein said oxidation is carried out at a temperature of from about 70° to 150° C.

6. Process according to any one of claims 1, 2 or 3, wherein said ester is of the formula:

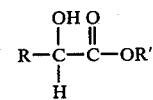

wherein R' represents an alkyl group of from 1–8 carbon atoms, a cycloalkyl group of from 5–8 carbon atoms in the ring, a phenyl or a naphthyl group.

7. Process according to any one of claims 1, 2 or 3, wherein R represents a phenyl, naphthyl, pyridyl, furyl or thienyl group, or such group carrying a Cl, $NO_2$, alkoxy of from 1–8 carbon atoms, or alkyl of from 1–8 carbon atoms, as a substituent thereon.

8. Process according to any one of claims 1, 2 or 3, wherein said cobalt catalyst is introduced as a soluble cobalt salt of a saturated aliphatic acid.

* * * * *